United States Patent [19]
Taro et al.

[11] 4,103,224
[45] Jul. 25, 1978

[54] MICRO-WAVE HYGROMETER

[75] Inventors: Miura Taro, Tokyo; Yamamoto Takahiro, Yachiyo; Suzuki Makoto, Tokyo; Nakai Shinya, Ichikawa, all of Japan

[73] Assignee: TDK Electronics Co., Ltd., Tokyo, Japan

[21] Appl. No.: 802,210

[22] Filed: May 31, 1977

[30] Foreign Application Priority Data

Jul. 7, 1976 [JP] Japan .................... 51/79863

[51] Int. Cl.² ............................................ G01R 27/04
[52] U.S. Cl. .................... 324/58.5 C; 73/29; 73/336.5
[58] Field of Search ............ 324/58.5 C, 58.5 A, 324/58.5 R; 73/29, 73, 336.5, 336

[56] References Cited

U.S. PATENT DOCUMENTS

| 2,792,548 | 5/1957 | Hershberger | 324/58.5 C |
| 3,492,568 | 1/1970 | Johnson | 324/58.5 A |
| 3,946,308 | 3/1976 | Miura et al. | 324/58.5 C |

FOREIGN PATENT DOCUMENTS

| 381,039 | 8/1973 | U.S.S.R. | 324/58.5 C |

*Primary Examiner*—Stanley T. Krawczewicz
*Attorney, Agent, or Firm*—Allison C. Collard

[57] ABSTRACT

A micro-wave hygrometer having a dielectric resonator, a micro-wave transmitter and receiver to and from the dielectric resonator, and an electro-static shield surrounding said dielectric resonator and a support supporting the dielectric resonator at the portion where the electric field is small. The humidity of air and/or gas can be measured by measuring the value Q of the resonator for micro-wave energy, or the loss of micro-wave energy.

6 Claims, 13 Drawing Figures

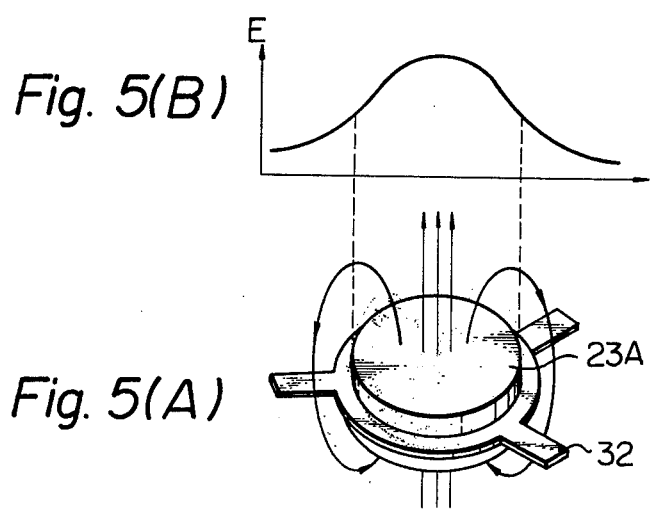
Fig. 5(B)
Fig. 5(A)
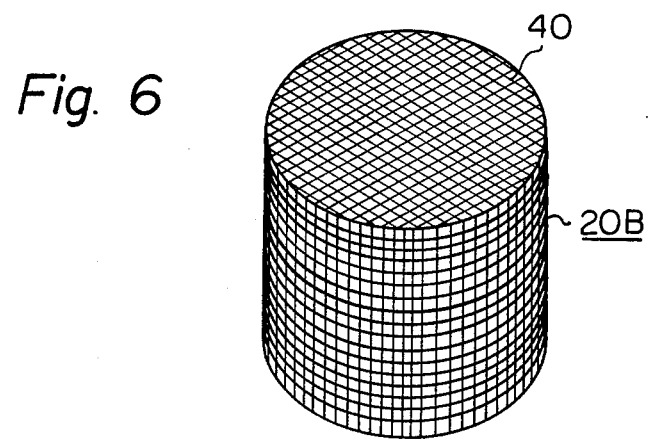
Fig. 6

MICRO-WAVE HYGROMETER

BACKGROUND OF THE INVENTION

The present invention relates to an apparatus for measuring the humidity of air and/or another gas, in particular, relates to a micro-wave hygrometer using micro-wave energy and providing an electrical output relating to the measured humidty.

It has been well known that the loss of the micro-wave energy due to the presence of water molecules ($H_2O$) in the air depends upon the air-pressure, the temperature of the air, and the partial pressure of the water vapour. Accordingly, the measurement of the micro-wave loss in the air, the air pressure, and the temperature of the air can provide the resultant partial pressure of the water vapour, that is to say, the humidity of the air, as proposed in the U.S. Pat. No. 2,792,548.

However, the U.S. Pat. No. 2,792,548 has the following disadvantages due to the use of a cavity resonator. The first disadvantage is that accurate measurement of the humidity is difficult because the pressure and/or the temperature might be different between in the cavity and in the air. The second disadvantage is that the measured humidity may have the secular variation since the metal wall of the cavity can be corroded by the moist air.

Another prior humidity meter is U.S. Pat. No. 3,946,308, which uses a dielectric resonator instead of the cavity resonator. However, it has the disadvantage that the measured humidity value drifts because of the presence of body which causes a loss in the micro-wave energy, located near the dielectric resonator. A body of an operator or another dielectric material might cause such drift.

SUMMARY OF THE INVENTION

It is an object, therefore, of the present invention to overcome the disadvantages and limitations of the prior humidity meters by providing a new and improved micro-wave hygrometer.

The above and other objects are attained by a mictowave hygrometer having a shield housing having a small hole for the flow of the air but preventing the radiation of micro-wave energy, a dielectric resonator mounted in the housing, a support for supporting said dielectric resonator in said housing at the portion where the electric field is weak, a pair of antennae provided in said housing for transmitting and receiving the micro-wave energy through said dielectric resonator.

BRIEF DESCRIPTION OF THE DRAWINGS

The foregoing and other objects, features, and attendant advantages of the present invention will be appreciated as the same become better understood by means of the following description and the accompanying drawings wherein;

FIG. 5(A) is the explanatory drawing for the explanation of the operation of the micro-wave hygrometer in FIG. 4;

FIG. 5(B) is the curve showing the electrical field in the radial direction of the dielectric resonator;

FIG. 6 is the embodiment of the electro-static shield;

DETAILED DESCRIPTION OF THE PREFERRED EMBODIMENTS

First, the operational principle of the micro-wave type hygrometer will be explained in accordance with FIG. 1, which is similar in structure to that in U.S. Pat. No. 2,792,548, for the easy understanding of the present invention.

Figure 1:
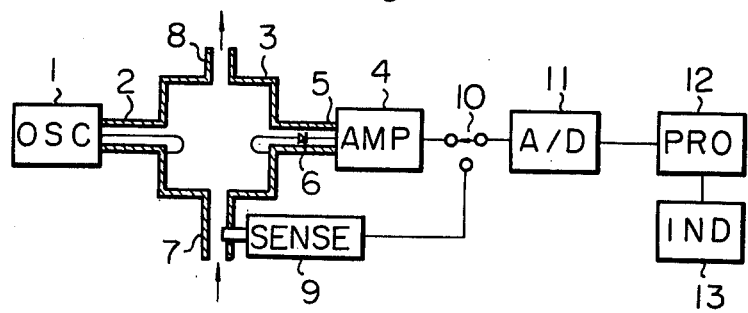
FIG. 1 is the blockdiagram showing the electrical circuitry of the prior micro-wave humidity meter.

In FIG. 1, the sweep oscillator 1 provides micro-wave energy to the cavity resonator 3 through the co-axial cable 2. The amplifier 4 is also connected to the cavity resonator 3 through the coaxial cable 5 and the diode (detector) 6. The cavity resonator 3 has an air inlet 7 and an air outlet 8, and the air flows through the cavity resonator 3 as shown by the arrows. The temperature sensor 9 provided at the inlet 7 measures the temperature of the air. The outputs of said amplifier 4 and the temperature sensor 9 are alternately applied to the analog-digital convertor 11 through the switch 10, in the form of digital signal. The output of the analog-digital converter 11 is processed by the processor 12, the result of which is applied to the indicator 13 for the indication of the measured humidity.

In the above structure, micro-wave energy modulated with a predetermined frequency from the sweep oscillator 1 is applied to the cavity resonator 3 through the coaxial cable 2 on the condition that the temperature and the pressure of the air in the cavity are known. Said microwave enegy is attenuated in the cavity 3 depending upon the pressure, temperature, and the humidity of the air in the cavity 3. The attenuated micro-wave energy which provides the information of the humidity in the cavity, is picked up by the detector 9, which applies an output signal relating to the amplitude of the micro-wave energy in the cavity to the amplifier 4. It is assumed that the micro-wave energy is modulated with the audio frequency for the sake of the easy processing. The output of the amplifier 4 is applied to the processor 12 through the switch 10 and the analog-digital convertor 11. The output of the temperature sensor 9 is also applied to the processor 12 through the switch 10 and the analog-digital convertor 11. The processor 12 calculates the humidity from the information applied to the same by calculating the change of loss of the micro-wave energy in the cavity 3 or the change of the Q of the cavity 3. The humidity calculated by the processor 12 is indicated at the indicator 13.

However, the humidity meter in FIG. 1 has the disadvantages mentioned before, due to the usage of the cavity resonator.

Figure 2:
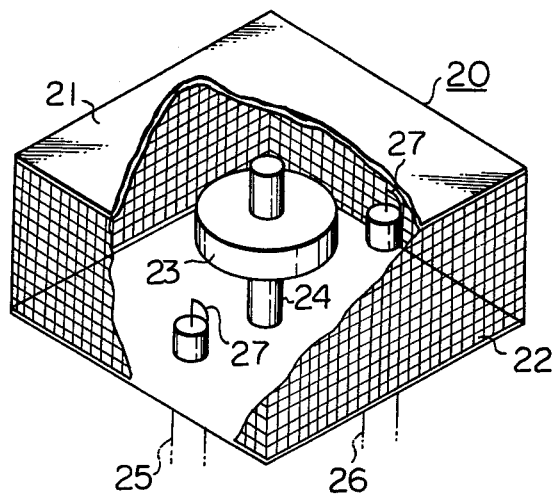
FIG. 2 is the perspective view of the embodiment of the present humidity meter.

FIG. 2 is the perspective view of the hygrometer according to the present invention. In the figure, the electro-static shield 20 has a pair of metal plates 21 on the top and the bottom surfaces, and the metal net 22 on the side surfaces. The dielectric resonator 23 of thin circular disk form is supported at the center of the disk by the support 24 in the shield 20. A pair of coaxial cables 25 and 26 pass through the bottom surface of the shield 20, and a loop antenna 27 are provided at the extreme end of the coaxial cables 25 and 26. The loop antenna 27 is in the form of a curved inner conductor of a coaxial cable, and the end of the loop antenna is electrically connected to the outer conductor of the corresponding coaxial cable. The material of the metal plate 21 and the metal net 22 is a conductive metal like copper or brass, and the density of the net is sufficient so as not to allow the micro-wave energy escape through the net. The experiment shows that the net of forty meshes (40 lines in every inch) is enough for micro-wave of 9 $GH_z$. The material of the dielectric resonator 23 is, for instance, a ceramic having a large dielectric constant, such as a ceramic the main component of which is the mixture of $M_gTiO_3$, $TiO_2$, and $CaTiO_3$. Of course other materials like styrene resin or polyester resin are possible. The material of the support 24 is for instance a ceramic in which the micro-wave energy is little attenuated, but of course another dielectric material and/or conductor can be used for that support 24.

Figure 3B:
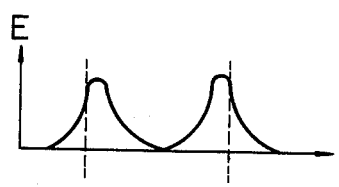
FIG. 3(B) is the curve showing the electrical field in the radial direction of the dielectric resonator.
Figures 3A, 3C:
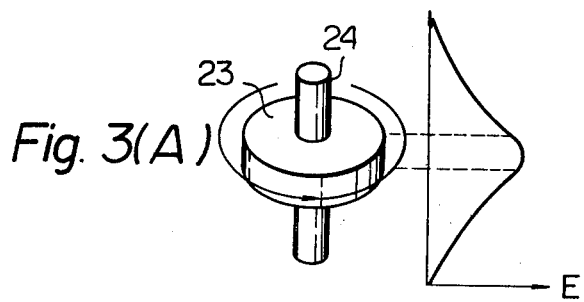
FIG. 3(A) is the explanatory drawing for the explanation of the operation of the present micro-wave hygrometer.
FIG. 3(C) is the curve showing the electrical field in the axis direction of the dielectric resonator.

In the structure of FIG. 2, when micro-wave energy is applied to the dielectric resonator 23 through the coaxial cable 25, the dielectric resonator 23 is electromagnetically coupled with the loop antenna 27, and a magnetic field occurs in the direction perpendicular to the loop. In another words, an electric field occurs in the direction parallel to the current in the loop antenna. Accordingly, the dielectric resonator 23 resonates in the $TE°_{01\delta mode}$, which is the combination of the $TE°_{010}$ mode and the $TE°_{011}$ mode, as shown in FIG. 3(A). The arrow of FIG. 3(A) shows the direction of electric flux. The strength of the electric field in the case is shown in FIG. 3(B) and FIG. 3(C), which shows that the electric field is maximum near the edge of the disk and is weakened apart from there. And the electric field is almost zero at the center of the disk as shown in FIG. 3(B). Therefore, the support 24 is connected to the resonator 23 at the center of the disk and fixes the disk to the shield 20. That structure minimizes the loss of the micro-wave energy in the support 24, since the disk is supported at the center of the disk where the electric field is almost zero. And the electric field from the dielectric resonator 23 is locked within the shield 20. The micro-wave energy outside of the dielectric resonator in the shield 20 is attenuated by the vapour involved in the air in the shield 20. The micro-wave energy thus attenuated is picked up by the other antenna and applied to the outer device (not shown) through the other coaxial cable 26, and is processed to indicate the humidity of the air through detection, amplification, and/or analog-digital conversion.

It should be appreciated that the hygrometer in FIG. 2 is surrounded by the net of the shield 20, and so the air can easily flow in and out of the shield 20, thus no forced circulation of the air is necessary. All that is necessary is merely put the apparatus in the air to be measured, so the present hygrometer can measure the humidity of still air. Further, the response time of the present hygrometer is very short, (the response time can be shortened theoretically to 10 μs), so the present hygrometer can follow sudden change of humidity. The secular variation of the measured value is very small in the present invention, since the dielectric resonator made of ceramic is chemically very stable as it is fired at high temperature. The typical characteristics of the ceramic is 20–30 of the dielectric factor and 0.5 ppm/° C of the temperature coefficient. Since the dielectric factor of the resonator 23 is relatively large, a hygrometer of small size can be obtained, and the thermal equilibrium condition between the surrounding air and the hygrometer can be obtained in a short time. Further, since the temperature coefficient of the dielectric resonator 23 is small, the measured error due to the change of the temperature is small and accurate measurements can be performed.

The sensitivity of the hygrometer depends upon the structure of the support of the dielectric resonator 23, and it should be appreciated that the present dielectric resonator 23 is supported at the portion where the electric field is the minimum so that the micro-wave energy can saturate the shield 20 and the loss in the support 24 is minimum, thus the sensitivity of the present hygrometer is very high.

Some modifications of the structure of FIG. 2 are possible to those skilled in the art. For instance, only a part of the side wall of the shield 20 can be metal net, instead of the whole side wall being composed of metal net. Further, instead of the metal net at the side wall, a top and/or a bottom surface 21 can have a window covered by metal net for the air circulation.

Figure 4:
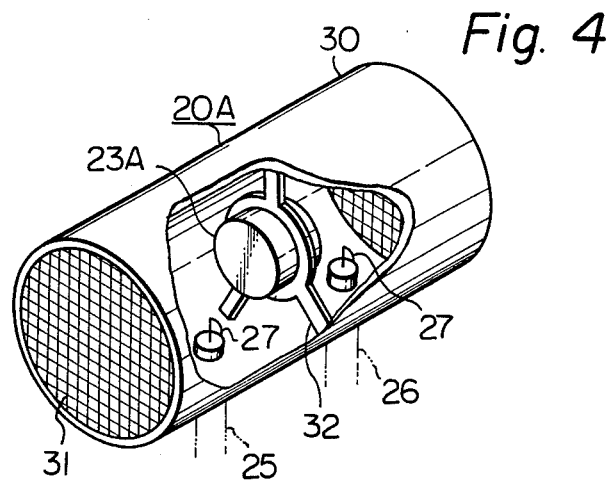
FIG. 4 is the perspective view of the second embodiment of the micro-wave hygrometer according to the present invention.

FIG. 4 shows the perspective view of the second embodiment of the present hygrometer. In this embodiment, the electrostatic shield 20A has a cylindrical metal pipe 30 and a pair of circular metal nets 31 provided at both the ends of said pipe 31. A thin circular dielectric resonator 23A is mounted in said pipe 30 by the support 32 which has three legs for fixing itself and the dielectric resonator. A pair of loop antenna 27 are provided at the extreme ends of the coaxial cables 25 and 26 which pass through the pipe 30.

In the structure of FIG. 4, micro-wave energy applied to the dielectric resonator 23A through one of the coaxial cables generates a magnetic field in the direction perpendicular to the loop of the antenna 27. In another words, an electric field parallel to the current in the loop antenna 27 is generated, and thus the dielectric resonator 23 is put in the resonance condition in the $TM°_{010}$ mode as shown in FIG. 5(A), where the arrows show the direction of the electric field. FIG. 5(B) shows the curve of the strength of the electric field. It should be noted from FIG. 5(B), that the electric field is maximum at the center of the disk of the resonator and decreases apart from there in the radial direction. Therefore, the electric field is not strong at the circumferential portion of the resonator. The support 32 supports the resonator 23A at that circumferential portion so that the loss of micro-wave energy in the support is small, and the most of the micro-wave energy emanating from the dielectric resonator 23 can fill the surrounding air in the shield.

The hygrometer in FIG. 4 provides similar results to those of the hygrometer in FIG. 2, further, the embodiment in FIG. 4 is more suitable to measure the humidity in a pipe for supplying or exhausting a gas to a large room. It should be appreciated that the support 32 can be in any form so long as it does not prevent the flow of the air.

FIG. 6 shows another structure of an electrostatic shield, in which the shield 20B has a cylindrical metal net and a pair of circular metal nets 40. The hygrometer having the shield 20B in FIG. 6 together with dielectric resonator and a pair of antenna can provide similar results to those of the embodiments in FIG. 2 and FIG. 4.

Figures 7A, 7B:
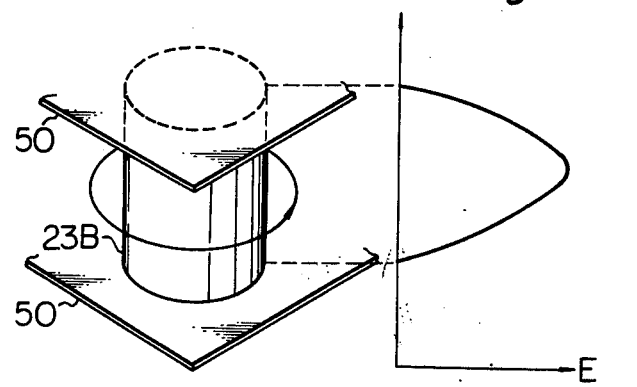
FIG. 7(A) is the perspective view of another embodiment of the hygrometer according to the present invention.
FIG. 7(B) is the curve showing the electrical field in the structure of FIG. 7(A)

FIG. 7(A) shows another embodiment of the structure of a dielectric resonator. In the figure, the resonator 23B is in a column or cylindrical form, at both the ends of which a pair of metal shield plates 50 are provided. Said plates 50 double as a support of the resonator 23B. The microwave energy in this embodiment resonates in the $TE°_{011}$ mode, and the arrow in the figure shows the direction of the electric field. FIG. 7(B) shows the curve of the electric field in case of the $TE°_{011}$ mode. It should be appreciated from FIG. 7(B) that the electric field is the maximum at the center of the column in the axial direction of the resonator and decreases apart from there, and said electric field is zero at the ends of the column. The dielectric resonator in FIG. 7(A) can replace the resonator in FIG. 2 or FIG. 4 subject to the antennae 27 being excited in the $TE°_{011}$ mode. The resonator in FIG. 7(A) can be mounted in the shield in FIG. 6, where the resonator is supported by the shield plates 50.

Figure 8:
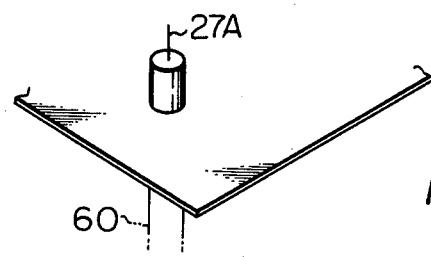
FIG. 8 and FIG. 9 show the embodiments of the antennae according to the present invention.
Figure 9:
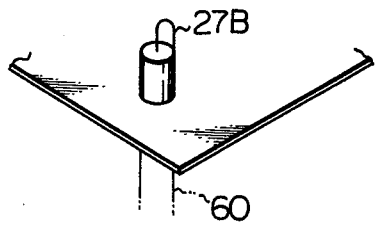

FIG. 8 and FIG. 9 show other embodiments of an antenna according to the present invention. FIG. 8 shows a bar type antenna 27A where the inner conductor of a coaxial cable extends straight up. The antenna 27B in FIG. 9 is U-shaped where the inner conductor of a coaxial cable is formed in that shape and the extreme end of the U-shape is connected to the outer conductor of a coaxial cable. Those antennae 27A and 27B can replace the antennae 27 in FIGS. 2 and 4 as long as the direction of those antennae 27A and 27B coincides with that of the electric field resonating in a dielectric resonator.

It should be appreciated that the combination of the shield 20 in FIG. 2 and the dielectric resonator 23A in FIG. 4, or the combination of the shield 20A in FIG. 4 and the dielectric resonator 23 in FIG. 2 are also possible. Further, the net on the shield in the embodiments mentioned above can be replaced by a bulk metal plate having a small hole for the flow of air but preventing the radiation the micro-wave energy. A coaxial cable can also be replaced by another transmission line for the input and the output of the micro-wave energy to and from the dielectric resonator. The shape of a dielectric resonator is not restricted to the disclosed disk or column shape, but other shapes like a polygonal pillar shape are possible.

Since the present humidity meter or hygrometer is not affected by chemical reactions or moisture, the application field of the present hygrometer is expanded to environments with high temperature and/or high humidity, which prior hygrometers can not measure. The present hygrometer is most suitable for controlling an environment precisely in the chemical industry or printing industry which require accurate and precise control of humidity.

From the foregoing it will now be apparent that a new and improved hygrometer has been found. It should be understood of course that the embodiments disclosed are merely illustrative and are not intended to limit the scope of the invention. Reference should be made to the appended claims, therefore, rather than the specification as indicating the scope of the invention.

Finally, the reference numerals referred to in the specification are listed below.
1: sweep oscillator
2: coaxial cable
3: cavity resonator
4: amplifier
5: coaxial cable
6: detector
7: air inlet
8: air outlet
9: temperature sensor
10: switch
11: analog-digital convertor
12: processor
13: indicator
20, 20A, 20B: electro static shield
21: shield plate
22, 31, 40: net
23, 23A, 23B: dielectric resonator
24: support
25, 26: coaxial cable
27, 27A, 27B: loop antenna
32: support.

What is claimed is:

1. A micro-wave hygrometer comprising a shield housing having a small hole for the flow of the air but preventing the radiation of the micro-wave energy, a dielectric resonator mounted in the housing, a support for supporting said dielectric resonator in said housing at the portion where the electric field is weak, a pair of antennae provided in said housing for transmitting and receiving the micro-wave energy through said dielectric resonator.

2. A hygrometer according to claim (1), wherein said dielectric resonator is in a thin circular disk form excited in the $TE°_{01\delta}$ mode, and is supported at the center of the disk.

3. A hygrometer according to claim (1), wherein said dielectric resonator is in a disk shape excited in the $TM°_{010}$ mode, and is supported at the circumferential portion of the disk.

4. A hygrometer according to claim (1), wherein said dielectric resonator is in a column shape excited in the $TE°_{011}$ mode, a pair of shield plates provided at both the longitudinal ends of the resonator supports the resonator.

5. A hygrometer according to claim (1), wherein said shield housing has at least a metal net wall.

6. A hygrometer according to claim (5), wherein said net has at least 40 metal lines in every inch.

* * * * *